(12) United States Patent
Wines

(10) Patent No.: US 12,220,343 B2
(45) Date of Patent: Feb. 11, 2025

(54) STOMA TEMPLATE AND METHOD OF FABRICATING A CUSTOM OSTOMY SKIN BARRIER

(71) Applicant: Hollister Incorporated, Libertyville, IL (US)

(72) Inventor: James P. Wines, Algonquin, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

(21) Appl. No.: 18/697,828

(22) PCT Filed: Aug. 31, 2022

(86) PCT No.: PCT/US2022/042160
§ 371 (c)(1),
(2) Date: Apr. 2, 2024

(87) PCT Pub. No.: WO2023/064049
PCT Pub. Date: Apr. 20, 2023

(65) Prior Publication Data
US 2024/0315865 A1      Sep. 26, 2024

Related U.S. Application Data

(60) Provisional application No. 63/254,239, filed on Oct. 11, 2021.

(51) Int. Cl.
*A61F 5/443*     (2006.01)
(52) U.S. Cl.
CPC .................................. *A61F 5/443* (2013.01)
(58) Field of Classification Search
CPC ....................................................... A61F 5/443
(Continued)

(56) References Cited

U.S. PATENT DOCUMENTS

| 4,095,599 A | * | 6/1978 | Simonet-Haibe | ....... A61F 5/445 604/336 |
| 4,681,574 A | * | 7/1987 | Eastman | ................. A61F 5/443 604/344 |

(Continued)

FOREIGN PATENT DOCUMENTS

| DE | 9105753 U1 | 7/1991 |
| EP | 1275357 A2 | 1/2003 |

(Continued)

OTHER PUBLICATIONS

International Preliminary Report on Patentability for PCT/US2022/042160, dated Apr. 16, 2024, 9 pages.

*Primary Examiner* — Andrew J Mensh
(74) *Attorney, Agent, or Firm* — Klintworth & Rozenblat IP LLP

(57) ABSTRACT

A stoma template comprising a body portion having opposing inside and outside edges and opposing first and second sides. The inside edge can define an opening extending through the body portion between the first and second sides. The first side can have a plurality of flexible segments extending between the inside and outside edges. The plurality of flexible segments can be separated from one another by grooves and have a sticky surface along the first side of the body portion. At least a portion of a flexible segment can be peelable away from the opening to form a peeled portion. The peeled portion can be foldable over a respective unpeeled portion of the flexible segment and be adherable to the sticky surface. The inside edge of the body portion can be pulled back by the peeled portion and the opening can be expanded.

11 Claims, 4 Drawing Sheets

(58) Field of Classification Search
USPC .......................................................... 604/336
See application file for complete search history.

(56) References Cited

U.S. PATENT DOCUMENTS

| | | | |
|---|---|---|---|
| 6,659,989 B1* | 12/2003 | Otto ........................ | A61F 5/445 |
| | | | 604/339 |
| 8,708,987 B2 | 4/2014 | Cramer et al. | |
| 8,795,384 B2 | 8/2014 | Nelson et al. | |
| 10,449,082 B2 | 10/2019 | Johnsen | |
| 2003/0060786 A1* | 3/2003 | Olsen ....................... | A61F 5/448 |
| | | | 604/339 |
| 2004/0111072 A1* | 6/2004 | McKissick .............. | A61F 5/445 |
| | | | 604/332 |
| 2008/0167729 A1* | 7/2008 | Nelson .................. | A61F 2/0063 |
| | | | 623/23.72 |
| 2013/0261575 A1* | 10/2013 | Kiyoshi .............. | A61B 5/1075 |
| | | | 156/64 |
| 2020/0038226 A1* | 2/2020 | Botten .................... | A61F 5/443 |

FOREIGN PATENT DOCUMENTS

| | | | |
|---|---|---|---|
| EP | 0800804 | B2 | 10/2011 |
| EP | 2648662 | B1 | 4/2015 |

\* cited by examiner

STOMA TEMPLATE AND METHOD OF FABRICATING A CUSTOM OSTOMY SKIN BARRIER

This is a National Stage Application of International Patent Application No. PCT/US2022/042160, filed Aug. 31, 2022, which claims the benefit of and priority to U.S. Provisional Application No. 63/254,239, filed Oct. 11, 2021, the entirety of which is incorporated fully herein by reference.

BACKGROUND

The present disclosure relates to ostomy appliances, and more particularly to a template for forming an ostomy skin barrier for improved fit around a surgically created stoma.

Ostomy pouches for the collection of body waste output from a stoma are well known and used by individuals who have had surgery such as a colostomy, ileostomy or urostomy. Ostomy pouches are generally attached to a user via an ostomy skin barrier, which is configured to seal against peristomal skin surfaces and protect the peristomal surfaces from exposure to stomal effluent. However, the shape and size of stomas can vary among patients and providing a single skin barrier which can effectively seal against the peristomal surfaces of differently sized or shaped stomas can be particularly challenging.

Devices such as template sheets, adhesive wafers and implantable skin grafts in various forms are generally known and used to fabricate a skin barrier to better corresponds to the shape and size of individual stomas. Such devices and solutions however are either invasive, difficult to use and/or not precise from the standpoint of generating a customized skin barrier that closely matches the specific size and contours of a particular user's stomal region.

Accordingly, as will be recognized from the subject disclosure, there is a critical need in the art for a stoma template that is economical, simple to use and capable of fabricating a precisely sized and shaped skin barrier that closely seals around the stoma of different users. There is a further need in the art to provide such stoma template for multiple use.

SUMMARY OF THE DISCLOSURE

Embodiments presented herein are directed to a stoma template comprising a body portion having opposing inside and outside edges and opposing first and second sides. The inside edge of the stoma template can define an opening extending through the body portion between the first and second sides. The first side can have a plurality of flexible segments extending between the inside and outside edges. The plurality of flexible segments can be separated from one another by grooves and have a sticky surface along the first side of the body portion. At least a portion of a flexible segment of the plurality of flexible segments can be peelable away from the opening to form a peeled portion. The peeled portion can be foldable over a respective unpeeled portion of the flexible segment and be adherable to the sticky surface. The inside edge of the body portion can be pulled back by the peeled portion and the opening being expanded.

According to exemplary embodiments, the grooves along the first side of the body portion can comprise a series of perforations along their length. The plurality of flexible segments can have substantially straight opposing side edges that can extend from the inside edge to the outside edge of the body portion. The opposing side edges of adjacent flexible segments can define opposing side edges of one of the grooves. The plurality of flexible segments can be comprised of skin barrier material. The plurality of flexible segments can encircle the opening and radiate outward therefrom. The plurality of flexible segments can widen as they extend toward the outside edge of the body portion. The stoma template can further comprise a film to cover the first side of the body portion. The film can be adherable to the sticky surface. The body portion can be toroid-shaped wherein the opening can be centrally located.

Embodiments presented herein are further directed to methods of fabricating an ostomy skin barrier. According to such methods, a stoma template can be provided having a plurality of flexible segments along a first side between opposing inside and outside edges. The plurality of flexible segments can have a sticky surface and be separated from one another by grooves having perforations therein. A portion of at least one flexible segment of the plurality of flexible segments can be peeled outward and away from a central opening in the stoma template to form a peeled portion. The peeled portion can be folded over a respective unpeeled portion of the at least one flexible segment. The peeled portion can be pressed to the sticky surface of the unpeeled portion to cause the peeled portion and a portion of the unpeeled portion to stick together. The inside edge of the stoma template can be reconfigured to customize the opening to correspond to a perimeter of a stoma. The template can be placed alongside an ostomy skin barrier material. The skin barrier material can be cut to correspond to the stoma template. The cutting can form opposing inside and outside edges of the ostomy skin barrier whereby the opposing inside and outside edges of the ostomy skin barrier respectively correspond to the reconfigured inside edge and the outside edge of the stoma template.

According to exemplary embodiments, methods presented herein can further comprise placement of the stoma template alongside the stoma to identify which of the plurality of flexible segments to peel back and how much of the portion of at least one flexible segment should be peeled. An outline of the stoma template can be onto the ostomy skin barrier whereby the tracing can follow the reconfigured inside edge and the outside edge of the stoma template. A film can be cut to correspond to the stoma template. The film can be adhered to the first side of the stoma template along the sticky surface. The cutting can form opposing inside and outside edges of the film which can respectively correspond to the reconfigured inside edge and the outside edge of the stoma template.

Other objects, advantages and features of the present disclosure will be understood and appreciated by persons of ordinary skill in the art from consideration of the following specification taken in conjunction with the accompanying drawings.

DETAILED DESCRIPTION

Figure 1:
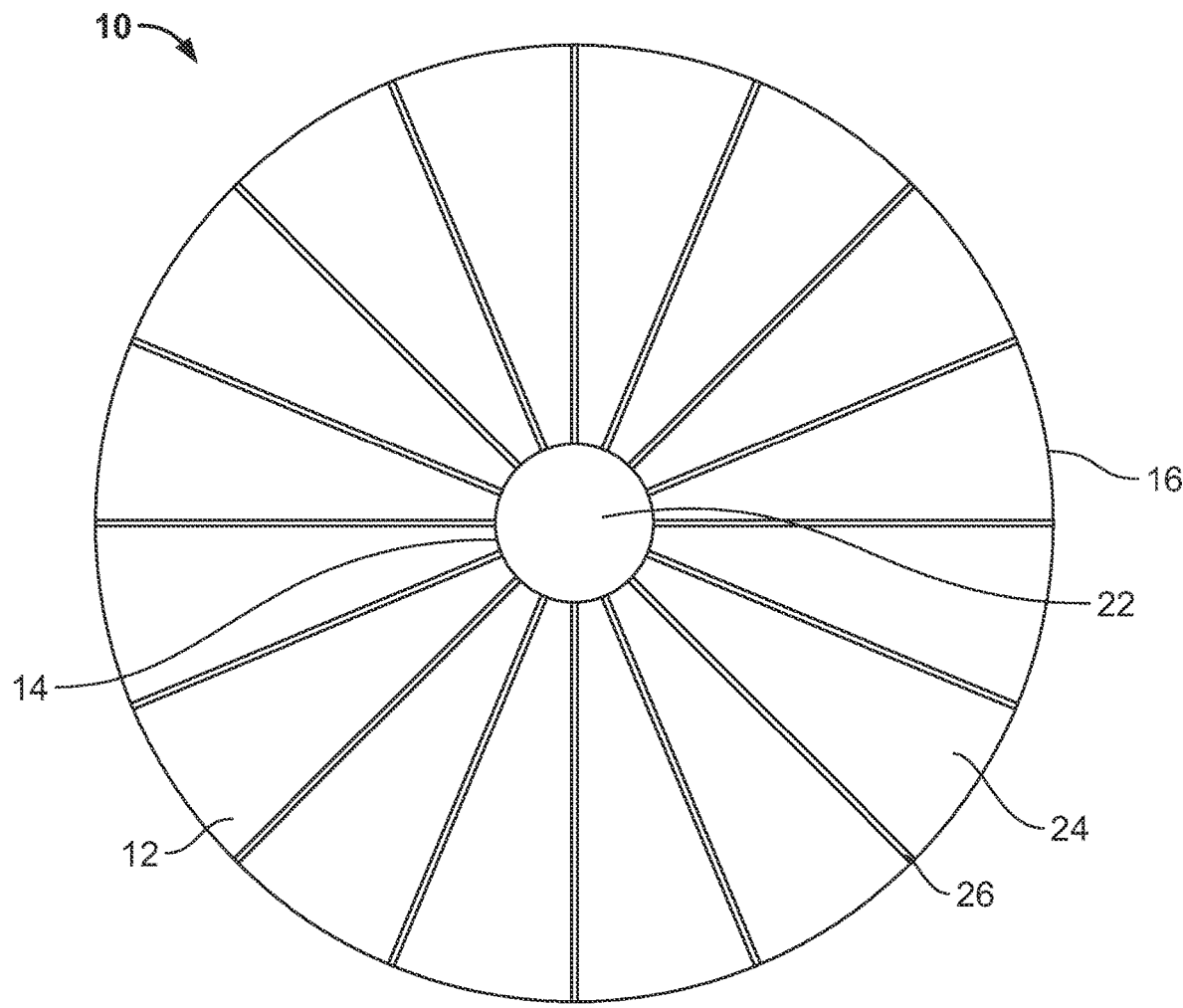
FIG. 1 is a plan view of a stoma template in a condition prior to use according to exemplary embodiments presented herein.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 2:
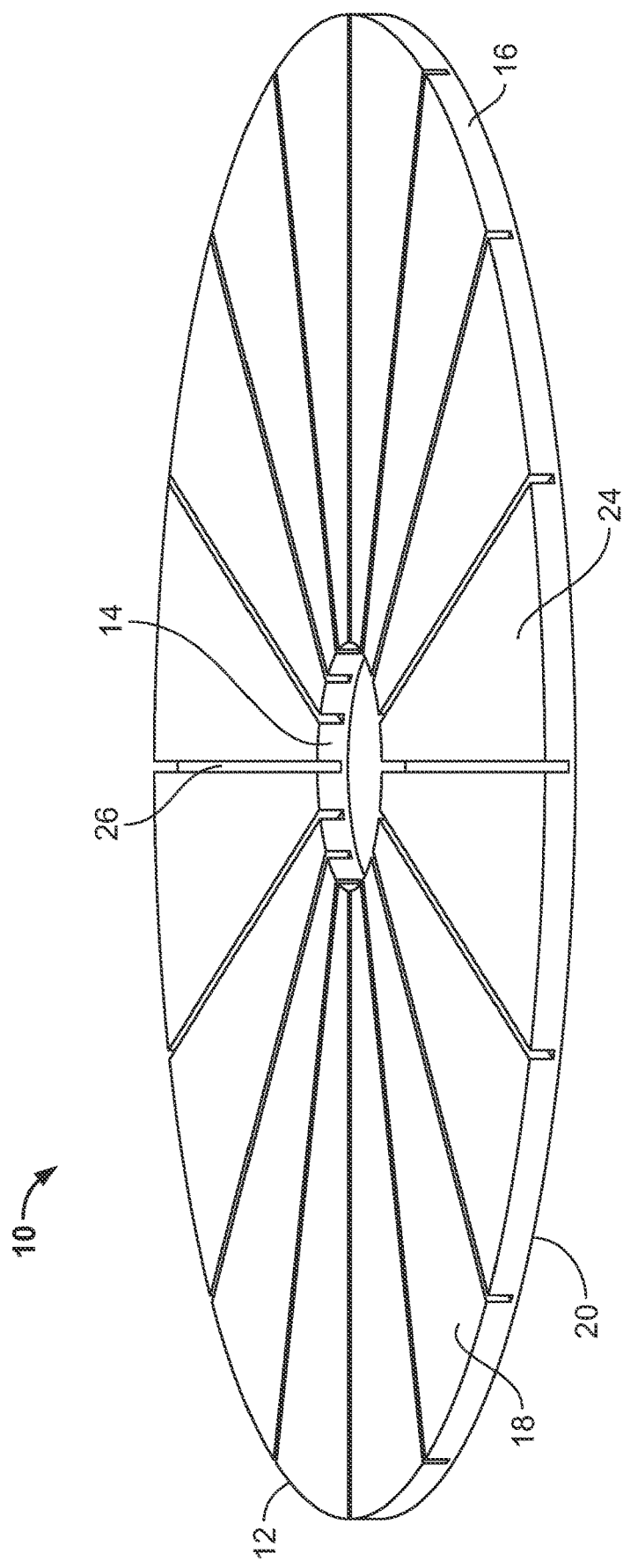
FIG. 2 is a perspective view of the stoma template of FIG. 1.

Referring now to the accompanying figures, and FIGS. 1-2 in particular, a stoma template 10 is shown according to exemplary embodiments in a condition prior to use. As shown schematically in FIGS. 1-2, stoma template 10 can be comprised of a body portion 12 having opposing inside and outside edges 14, 16 and opposing first and second sides 18, 20. According to exemplary embodiments, shown schematically in FIGS. 1-2, inside edge 14 can be arranged around and define an opening 22 extending through the template 10 between the first and second sides 18, 20 and body portion 12 can radially extend outward from opening 22. Opening can be circularly shaped and centrally located on template 10 as shown in FIGS. 1-2, however it will be understood that opening can have other shapes and locations along template 10 without limitation. As shown in FIG. 1, the outside edge 16 can have a greater circumference than the inside edge 14.

According to exemplary embodiments shown schematically in FIGS. 1-2, the first side 18 of body portion 12 can be comprised of a plurality of flexible segments 24 separated from one another by grooves 26 having perforations therein. As shown in FIGS. 1-2, flexible segments 24 can extend between the inside and outside edges 14, 16 of template 10. Flexible segments 24 can fully surround opening 22 and be equally sized and shaped as shown in FIGS. 1-2, although it will be understood that template 10 can have segments surrounding only around a portion of opening 22 or segments having multiple different shapes or sizes without departing from the novel scope of the subject invention. Flexible segments 24 can have substantially straight side edges and a substantially flat top surface which define the first surface of template 10. The opposing second side 20 of template 10 can comprise a backing layer.

According to exemplary embodiments shown schematically in FIGS. 1-2, flexible segments 24 can radiate outward from opening 22 such that the side edges of a segment diverge along their length as they extend toward the outside edge 16 of template 10 (by contrast, the side edges converging toward one another along their length as they extend inward from the outside edge 16 toward the inside edge 14 of template 10). Thus, as will be understood, an arc formed between first points along opposing side edges equally distanced from the inside edge 14 will have a first length, and an arc formed between second points equally distanced from the inside edge 14 at a greater distance from the first points will have a second length greater than the first length. Accordingly, as shown in FIGS. 1-2, flexible segments will widen as they extend toward outer edge 16 of template 10.

As shown schematically in FIGS. 1-2, grooves 26 can be comprised as channels defined between side edges of adjacent flexible segments 24 and can extend along the length of the side edges of adjacent segments between the inside and outside edges 14, 16 of template 10. Grooves can have a series of perforations through the body portion 12 which can facilitate separation of the flexible segments 24 upon being peeled back as described in additional detail below. It will be understood that the thickness and depth of grooves 26 (defined by the corresponding spacing and height of flexible segments 24) can vary but be configured to permit template 10 to have sufficient firmness and structure to avoid unintended tears or separation while also being capable of manipulation as explained in greater detail herein. Concurrently, it will be understood that the thickness of flexible segments 24 (between the first and second sides 18, 20 of template 10) can vary but be configured to provide sufficient rigidness so as not to unintentionally or uncontrollably fold while also being capable of having sufficient pliability to intended peeling and folding as explained in greater detail herein. Thus, by way of exemplification only, representative embodiments presented herein can have flexible segments 24 having a thickness on the order between 0.1 and 0.5 inches and grooves 26 having a depth on the order of 0.09 and 0.49 inches.

According to exemplary embodiments, stoma template 10 can be comprised of a flexible or moldable material, such as for example a stomal skin barrier material. Additionally, the first side 18 of template 10 can be comprised of applied with a sticky, tacky or adhesive surface coating. Together with the grooves 26, the flexible material and adhesive surface coating can enable portions of segments 24 adjacent opening 22 to be to be peeled back and folded over itself to create a customized template for use in making a custom-fitted skin barrier.

Figure 3:
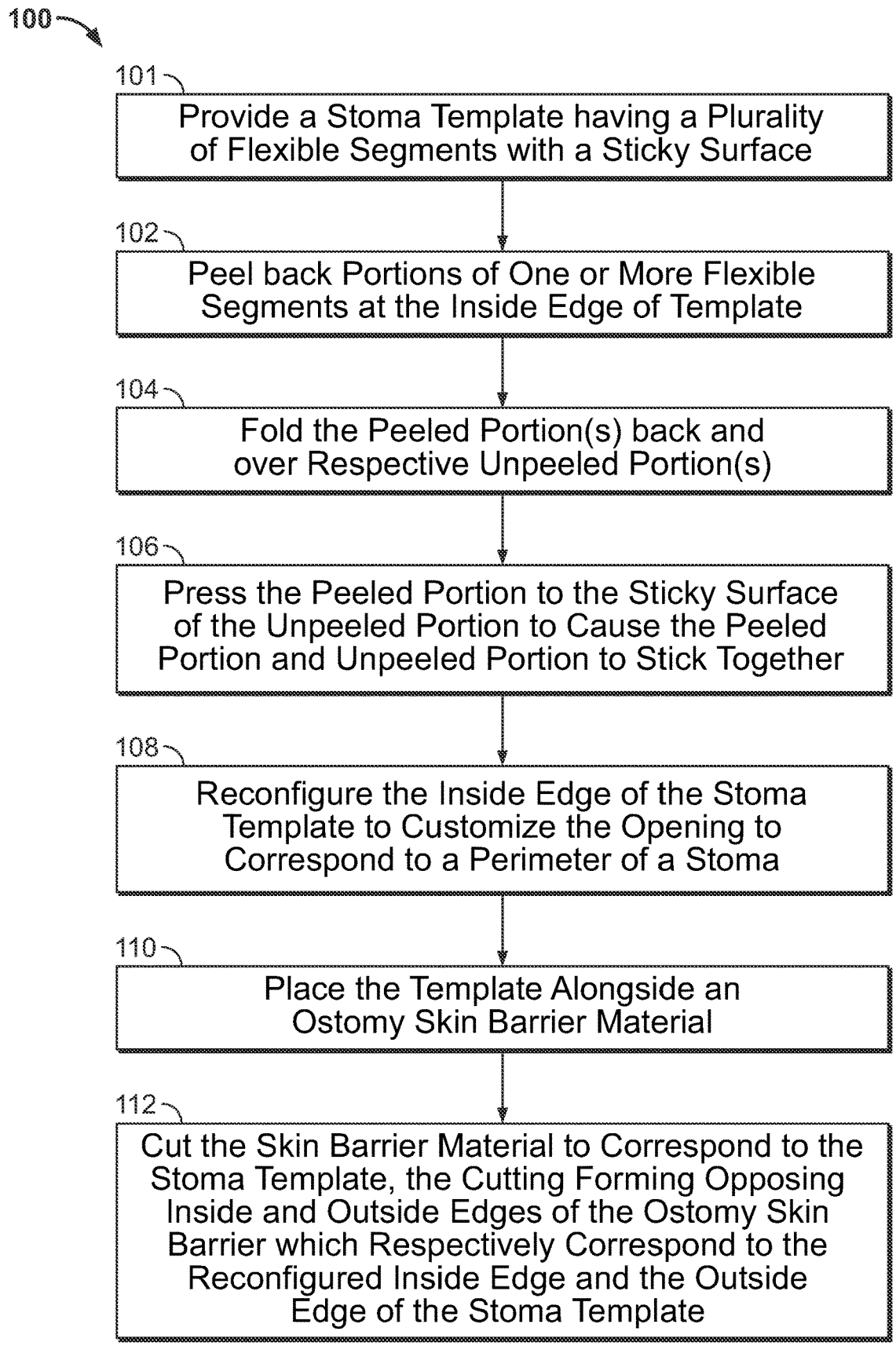
FIG. 3 is a flow diagram of a method according to exemplary embodiments presented herein.

More particularly, and with reference to FIG. 3, a method 100 of fabricating a stoma template is representatively illustrated. As shown in FIG. 3, stoma template can be provided 101 according to embodiments exemplified herein. In use a user can peel back 102 portions of one or more flexible segment 24 at the inside edge 14 of template 10 and fold 104 the peeled portion(s) back and over adjacent unpeeled portions of the respective one or more segments along the first side 18 of template 10. It will be recognized that upon peeling and folding a flexible segment over itself, that the sticky or tacky surface of the peeled and unpeeled portions can be oriented to face each other. According to exemplary embodiments, the peeled portion can then be pressed 106 onto the unpeeled portion for being adhered thereto. It will be recognized that such steps can cause opening 22 to be enlarged and reshaped in the respective area. More particularly, the inside edge of the stoma template can be reconfigured 108 in specific areas 32 to customize opening 22 to correspond to a perimeter of a user's stoma.

Figure 4:
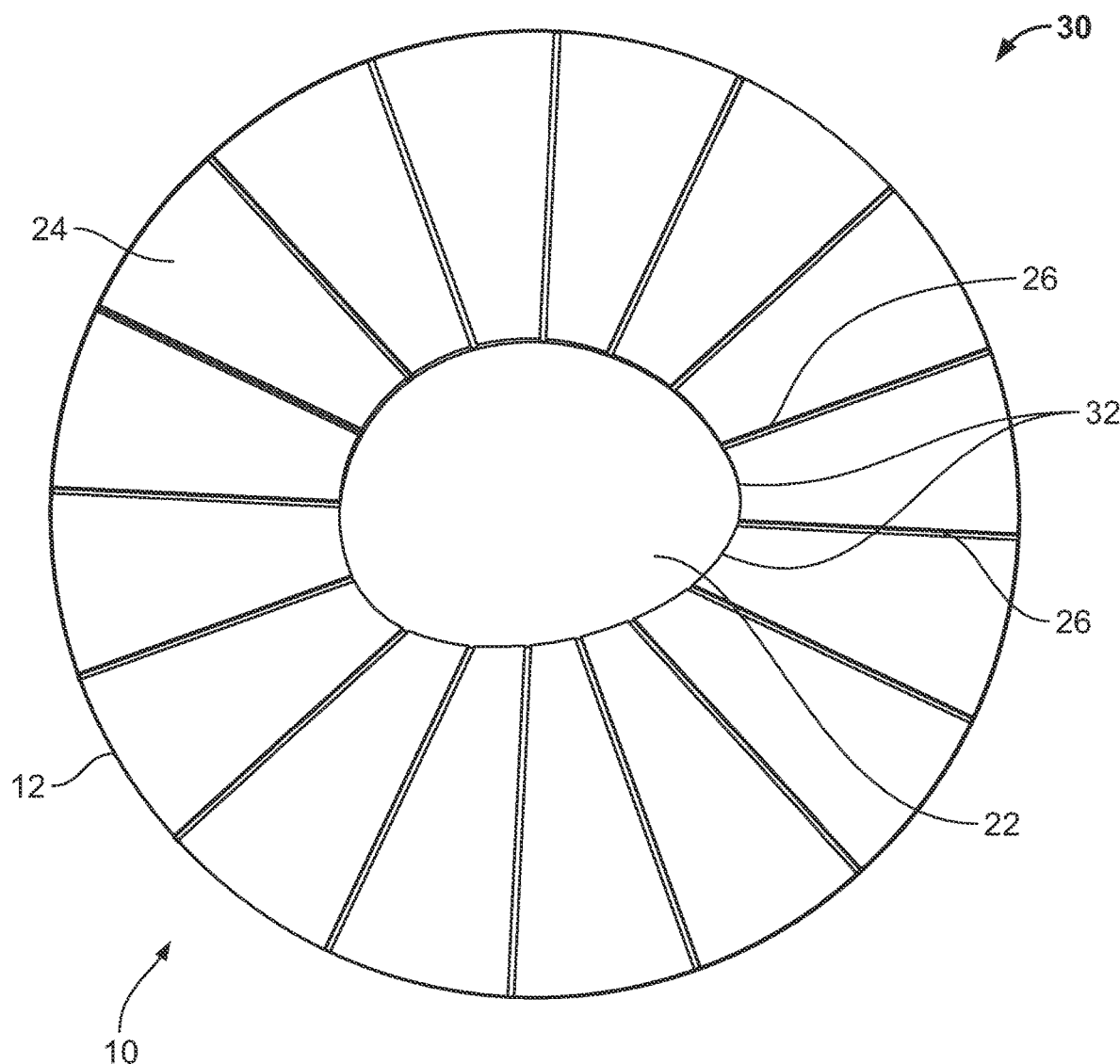
FIG. 4 is a plan view of a stoma template in a condition of use according to exemplary embodiments presented herein.

For exemplification, FIG. 4 illustrates a reconfigured stoma template 30 in a condition of use whereby portions of one or more flexible segments 24 have been pealed back to enlarge and reshape opening 22. As shown representatively in FIG. 4, and as best seen when compared to FIG. 1, opening 22 has been modified and made larger and to have an irregular shape formed by the inside edges 32 of certain flexible segments 24 being peeled back. In view of the fact that stomas can vary in shape and size between different users, it will be recognized that embodiments presented herein can be particularly useful to create a customized template that can be particularly suited for each individual user.

In customizing the template 10, users can hold the template up to the stoma and peel back certain segments 24 until a custom size or shape is achieved whereby the template 10 fits around the stoma and/or the stoma fits through opening 24. Embodiments presented herein can further provide for markings to be pre-applied along the first side 18 of template 10 at predetermined spacings around opening 10 so that a user can better gauge how far back to peel back certain foldable segments 24 and/or replicate a custom template. Users can also add markings themselves or trace the outline of the stoma along the first side 18 of template so that flexible panels 24 can be peeled and folded back the desired distance before being adhered to adjacent un-pealed portion(s).

Returning to FIG. 3, once a template 10 has been customized to a user's preference or need, the template can be used to fabricate a custom skin barrier. More particularly, the template 10 can be placed over or oriented against 110 a skin barrier material and the barrier material can be cut 112 to correspond to the size and shape of the template including along the modified inside edge around the custom opening and along the outside edge 16 of template 10. According to exemplary embodiments, an outline of the template can also be traced onto the barrier material with a drawing instrument before cutting to ensure that the shape and size are in accordance with a user's preference before cutting into the barrier material. It will be recognized that the cutting or tracing of the template 10 can follow the lines of the reconfigured inside edge and the outside edge 16.

According to exemplary embodiments presented herein, template 10 can be intended for single use or multiple uses. Where intended for multiple use, embodiments presented herein can additionally include a cover layer such as a film which can be placed over or applied to the first side 18 of template 10. Since the first side 18 has a sticky or tacky coating, the film can adhere thereto and cover the sticky side so that the template won't stick to other articles or trap debris. Cover layer can also include an adhesive or sticky surface to facilitate securing to template 10 and can further be configured for being cut to conform with the modified opening of the template 10.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A stoma template comprising:
   a body portion having opposing inside and outside edges and opposing first and second sides;
   wherein the inside edge defines an opening extending through the body portion between the first and second sides;
   wherein the first side has a plurality of flexible segments extending between the inside and outside edges, the plurality of flexible segments being separated from one another by grooves and having a sticky surface along the first side of the body portion, and
   wherein a least a portion of a flexible segment of the plurality of flexible segments is peelable away from the opening to form a peeled portion, the peeled portion being foldable over a respective unpeeled portion of the flexible segment and being adherable to the sticky surface, the inside edge of the body portion being pulled back by the peeled portion and the opening being expanded.

2. The stoma template of claim 1 wherein the grooves comprise a series of perforations along their length.

3. The stoma template of claim 1 wherein the plurality of flexible segments have substantially straight opposing side edges extending from the inside edge to the outside edge of the body portion, the opposing side edges of adjacent flexible segments defining opposing side edges of one of the grooves.

4. The stoma template of claim 1 wherein the plurality of flexible segments is comprised of skin barrier material.

5. The stoma template of claim 1 wherein the plurality of flexible segments encircle the opening and radiate outward therefrom, the plurality of flexible segments widening as they extend toward the outside edge of the body portion.

6. The stoma template of claim 1 further comprising a film to cover the first side of the body portion, the film being adherable to the sticky surface.

7. The stoma template of claim 1 wherein the body portion is toroid-shaped wherein the opening is centrally located.

8. A method of fabricating an ostomy skin barrier comprising:
   providing a stoma template having a plurality of flexible segments along a first side between opposing inside and outside edges, the plurality of flexible segments having a sticky surface and being separated from one another by grooves having perforations therein;
   peeling a portion of at least one flexible segment of the plurality of flexible segments outward and away from a central opening in the stoma template to form a peeled portion;
   folding the peeled portion over a respective unpeeled portion of the at least one flexible segment;
   pressing the peeled portion to the sticky surface of the unpeeled portion to cause the peeled portion and a portion of the unpeeled portion to stick together;
   reconfiguring the inside edge of the stoma template to customize the opening to correspond to a perimeter of a stoma;
   placing the template alongside an ostomy skin barrier material, and
   cutting the skin barrier material to correspond to the stoma template, the cutting forming opposing inside and outside edges of the ostomy skin barrier, the opposing inside and outside edges of the ostomy skin barrier respectively corresponding to the reconfigured inside edge and the outside edge of the stoma template.

9. The method of claim 8 further comprising placing the stoma template alongside the stoma and identifying which of the plurality of flexible segments to peel back and how much of the portion of at least one flexible segment should be peeled.

10. The method of claim 8 further comprising tracing an outline of the stoma template onto the ostomy skin barrier, the tracing following the reconfigured inside edge and the outside edge of the stoma template.

11. The method of claim 8 further comprising cutting a film to correspond to the stoma template and adhering the film to the first side of the stoma template along the sticky surface, the cutting forming opposing inside and outside edges of the film, the opposing inside and outside edges of the film respectively corresponding to the reconfigured inside edge and the outside edge of the stoma template.

* * * * *